US007384959B2

United States Patent
Davidson et al.

(10) Patent No.: US 7,384,959 B2
(45) Date of Patent: Jun. 10, 2008

(54) TREATMENT OF CONVULSIVE STATES

(75) Inventors: Elizabeth Janina Davidson, Herts (GB); Fiona Craig, Kent (GB)

(73) Assignee: Celltech Pharma Europe Limited, Berkshire (GB)

( * ) Notice: Subject to any disclaimer, the term of this patent is extended or adjusted under 35 U.S.C. 154(b) by 1007 days.

(21) Appl. No.: 10/148,535

(22) PCT Filed: Dec. 15, 2000

(86) PCT No.: PCT/GB00/04838

§ 371 (c)(1),
(2), (4) Date: Dec. 9, 2002

(87) PCT Pub. No.: WO01/43730

PCT Pub. Date: Jun. 21, 2001

(65) Prior Publication Data

US 2003/0162810 A1    Aug. 28, 2003

(30) Foreign Application Priority Data

Dec. 17, 1999 (GB) .................................. 9929981.0
Aug. 3, 2000 (GB) .................................. 0019061.1

(51) Int. Cl.
  *A61K 31/445* (2006.01)
(52) U.S. Cl. ..................................................... 514/315
(58) Field of Classification Search .................. 514/315
  See application file for complete search history.

(56) References Cited

U.S. PATENT DOCUMENTS 6,210,705 B1 *   4/2001   Mantelle et al.

FOREIGN PATENT DOCUMENTS

WO           97/27176      *  7/1997
WO       WO 97/27176          7/1997

OTHER PUBLICATIONS

Groos-Tsur et al., Epilepsy and ADHD: is methylphenidate safe and effective? J. Pediatr. Apr. 1997 130 (4) 670-674.*
Carlson et al., The Effects of Methylphenidate and lithium on attention and activity level, Journal of the Am. Acad. of Child and Adol. Psych. Mar. 1992 31 (2): 262-270.*
Aoyama, T., H. Kotaki, T. Sasaki, Y. Sawada, Y. Honda and T. Iga "Nonlinear kinetics of *threo*-methylphenidate enantiomers in a patient with narcolepsy and in healthy volunteers" *Eur. J. Clin. Pharmacol.* 44:79-84, 1993.
Ding, Y.-S., J.S. Fowler, N.D. Volkow, S.L. Dewey, G.-J. Wang, J. Logan, S.J. Gatley, N. Pappas "Chiral drugs: comparison of the pharmacokinetics of [$^{11}$C]*d-threo* and *l-threo*-methylphenidate in the human and baboon brain" *Psychopharmacology* 131:71-78, 1997.
Eckerman, D.A., Sheryl S. Moy, Ann N. Perkins, Kennerly S. Patrick and George R. Breese "Enantioselective Behavioral Effects of *threo*-Methylphenidate in Rats" *Pharmacology Biochemistry & Behavior* 40(4):875-880, 1991.

* cited by examiner

*Primary Examiner*—Shengjun Wang
(74) *Attorney, Agent, or Firm*—Saliwanchik, Lloyd & Saliwanchik

(57) ABSTRACT

Single enantiomer-threo-methylphenidate is useful in the therapy of a convulsant state, e.g. epilepsy, a bipolar disorder or narcolepsy. It may be administered topically.

3 Claims, No Drawings

TREATMENT OF CONVULSIVE STATES

This application is a National Stage Application of International Application Number PCT/GB00/04838, published, pursuant to PCT Article 21(2).

FIELD OF THE INVENTION

This invention relates to the treatment of epilepsy and other convulsive states, bipolar disorder and narcolepsy.

BACKGROUND OF THE INVENTION

Existing therapies for epilepsy have a variety of associated problems. For example, Epilim® (sodium valproate) is associated with liver dysfunction, including hepatic failure which has resulted in death, and has been found to interact with other drugs such as monoamine oxidase inhibitors. Drowsiness and sedation are among the side-effects on the CNS that have been noted for Epanutin® (phenytoin) and the benzodiazepine Valium® (diazepam). Drugs with the capacity to inhibit hepatic enzymes, such as cimetidine and omeprazole, have been found to reduce the clearance of benzodiazepines and can potentiate their action.

A further issue with existing anti-epilepsy treatments is patient compliance. Most of the oral treatments require repeated dosing within the day and it is not uncommon for doses to be omitted in error or inadvertently for logistical reasons.

Recent studies in humans have shown that anticonvulsant drugs have some efficacy in bipolar disorder (Scrip, No. 2484, Oct. 22nd 1999). The principal existing treatment, lithium, has drawbacks. For example, it is effective in only 50% of patients, monitoring of blood levels is required, and its use causes side-effects which lead to low compliance.

d,l-threo-methylphenidate (d,l-MPH) is available as Ritalin®. The ABPI Compendium of Data Sheets and Summaries of Product Characteristics (1999-2000) states that "Ritalin should be used with caution in patients with epilepsy as clinical evidence has shown that it can cause an increase in seizure frequency in a small number of such patients". See also the US Physicians' Desk Reference.

Patrick et al, J. Pharm. Exp. Ther. 24:152-158 (1987), indicates that the pharmacological action of d,l-MPH in the treatment of attention-deficit hyperactivity disorder (ADHD) is the property of the d-enantiomer (d-MPH), as no action on the part of the l-enantiomer (l-MPH) has been detected; see also Srinivas et al, Clin. Pharm. Ther. 52:561-8 (1992). It has also been found that, following oral dosing, the l-enantiomer is metabolised preferentially, such that plasma levels of the d-enantiomer are generally found to be higher than those of the l-enantiomer (Aoyama et al, Eur. J. Clin. Pharm. 44:79-84 (1993); Hubbard et al, J. Pharm. Sci. 78:944-7 (1989)), and that very little l-MPH enters the circulation or becomes available to the brain.

Intravenous administration of d,l-MPH has shown similar plasma levels of the two enantiomers for around 1.5 hours after dosing, after which the levels diverge (Srinivas, Pharm. Res. 10:14-21 (1993)). Ding et al, Psychopharmacology 131:71-78 (1997), has shown that l-MPH is detected in the brain after intravenous dosing.

WO-A-99/30694 discloses the topical application of d,l-MPH, using substantially zero order kinetics. An example of a topical composition comprises the drug in an adhesive base.

SUMMARY OF THE INVENTION

The present invention is based on the discovery that l-MPH may be used as an anticonvulsant, e.g. to treat patients suffering from epilepsy, or to treat bipolar disorder or narcolepsy, especially if delivered by a route other than oral. According to a second aspect of the invention, a topical composition comprises l-MPH and a suitable carrier.

It has surprisingly been found that the l-enantiomer possesses pharmacological activity broadly similar to that of the d-enantiomer and the racemate. The two enantiomers and the racemate induced similar stimulant effects in the Irwin Observation Test, including mainly excitation with signs of hypersensitivity to external stimulation, stereotypes with fore-paw treading, mydriasis and hyperthermia. Perhaps even more surprisingly for a stimulant, the l-enantiomer was found to possess anticonvulsant activity in an animal model, the Pentylenetetrazole (PTZ) Seizure Test, a property which was not shown by the d-enantiomer.

In the Irwin profile, sedation was not noted at the doses of l-MPH used in the PTZ test. Slight signs of stimulation were noted at doses having anti-convulsant effects but they were only slightly more marked than those seen with doses equivalent to the therapeutic dose of the racemate on a mg/kg basis. l-MPH was also found to antagonise barbital-induced sleep.

In addition, it has been found that, in the mouse, l-MPH was found not to be linked with liver damage as assessed by increased plasma level of alanine aminotransferase and microscopic examination for hepatic necrosis, and also that l-MPH had little or no effect on the activities of cytochrome $P_{450}$ sub-types 1A2, 2E1 and 3A4. At very high doses, some inhibition of cytochrome $P_{450}$ sub-types C8/9, 2C18/19 and 2D6 was found, but the concentrations required to inhibit enzyme activities (100 µM) were much greater than the maximum concentrations likely to be found in vivo and are therefore not likely to be clinically relevant.

These findings indicate a low potential for l-MPH to be associated with side-effects on the liver, sedation or significant drug interactions. Further, the adoption of topical dosing, with the potential for cutting down dosing frequency and for continuing therapy during sleeping hours, may remove the problem of patient compliance associated with existing anti-epilepsy treatments.

DESCRIPTION OF THE INVENTION

As indicated above, the PTZ model has shown that l-MPH delivered subcutaneously has anticonvulsant potential. To overcome the pre-systemic metabolism of l-MPH which occurs with oral administration and to counteract possible problems with compliance, l-MPH may be delivered in a topical presentation.

Topical application of drugs provides many advantages over conventional oral administration. Advantages include convenience, uninterrupted therapy, improved patient compliance, ease of discontinuation, elimination of presystemic metabolism, a high degree of control over blood concentration of the drug and improved overall therapy.

The l-MPH may be administered by the same means as is known for d,l-MPH, e.g. as described in WO-A-99/30694. In this way, substantially zero order kinetics, for delivery to the skin or mucosa, over a period of at least 10 hours, may be achieved.

The l-MPH may also be administered by any other conventional topical application method at any anatomical site. Conventional dosing parameters may be adopted, i.e. those which are known to or adapted to the practice of those skilled in the art.

Known topical formulations comprise emulsions, suspensions, solutions, creams, ointments and many other, with or without a vehicle such as a subcutaneous implant, suppository, patch or applicator. The most appropriate formulation and its delivery will be apparent to, or can readily be determined by, one skilled in the art. Similarly, the appropriate dosage can be determined, having regards to conventional factors such as the condition of the patient, the severity of the illness, the number and type of applications, etc. A typical dosage might comprise 10 to 200 mg l-MPH, to be applied 1-2 times per day.

The l-MPH will usually be used in substantially single enantiomer form, e.g. in at least 90%, preferably at least 95%, and most preferably at least 98% ee, with respect to d-MPH. Methods for preparing the active component used in this invention are known.

The following Tables report the results of the Irwin, PTZ and barbital interaction (sleep induction) tests. Description of these tests may be found in Psychopharmacologica, 13:222-257 (1968), Krall et al, Epilepsia 19:409-428 (1978), and Simon et al, J. Pharmacol, Paris 13:241-252 (1982). See also Roux et al, Phoenix international Pharmacology Reports Nos. D30.2061/2 and D99.021/2.

More particularly, Table 1 shows results of the Irwin test in the rat (3 rats per group), when l-MPH is administered by the subcutaneous route. At higher doses, of 64, 128 and 256 mg/ml, all rats exhibited further characteristics including sedation, fore-paw treading, stereotypes (head movements) and decreased muscle tone. In Table 1, the following apply:

+=slight; ++=moderate (X/N) indicates the number of rats showing the symptoms.

Observations were performed at 15, 30, 60, 120, 180 minutes and 24 hours after administration.

Hyperthermia and mydriasis were evaluated by comparison of the mean scores obtained in treated and control animals.

Tables 2a and 2b shows the effects of l-MPH, Ro 15-4513 (positive control, proconvulsant) and Diazepam (positive control, anticonvulsant) in the PTZ test, using 10 rats per group. Table 2a reports mean results based on animals showing the symptoms (minimum=3 animals). Table 2b reports results observed during 60 minutes. In these Tables:

Student's t Test: NS=Not Significant; *=p<0.05;  p<0.01; *=p<0.001

Fisher's Exact Test: No indication=Not Significant; =p<0.01; *=p<0.001

Table 3 shows the results of the barbital-interaction sleep induction test, again using 10 rats per group, for l-MPH and also d-MPH, d,l-MPH and caffeine. In Table 3, the following apply:

Student's t Test: NS=Not Significant; *=p<0.05; =p<0.01; *=<0.001

Fisher's Exact Test: (number of rats sleeping) No indication=Not Significant; +=$p$<0.05; ++=$p$<0.01; +++=$p$<0.001

(#): maximum=6 hours after barbital injection (taken 50 minutes after barbital injection).

TABLE 1

| | Dose (mg/kg) | | | |
|---|---|---|---|---|
| 2 | 4 | 8 | 16 | 32 |
| No change | Mydriasis + at 30' | Excitation + (2/3) at 30' Stereotypies (sniffing) (1/3) at 30' Mydriasis + at 30' | Excitation + (2/3) 60' → 120' Stereotypies (sniffing) (3/3) 30' → 120' Stereotypies (head movements) (1/3) 60' → 120' Mydriasis + at 30' | Excitation + (3/3) 15' → 30' Stereotypies (sniffing) (3/3) 15' → 120' ↑ Fear (3/3) 15' → 120' ↑ Reactivity to touch (3/3) 15' → 30' Mydriasis (++ 15' → 120') (+ at 180') Hyperthermia + at 30' and 120' |

TABLE 2a

| l-threo-Methylphenidate (mg/kg) s.c. −30 min | LATENCY TO CLONIC CONVULSIONS (sec) | | | LATENCY TO TONIC CONVULSIONS (sec) | | | LATENCY TO DEATHS (sec) | | |
|---|---|---|---|---|---|---|---|---|---|
| | mean ± s.e.m. | t value | % change from control | mean ± sem. | t value | % change from control | mean ± sem. | t value | % change from control |
| 0 | 546.0 ± 71.7 | — | — | 1170.0 ± 94.0 | — | — | 1302.0 ± 87.1 | — | — |
| 8 | 756.0 ± 105.0 NS | 1.652 | +38% | 1443.0 ± 198.2 NS | 1.245 | +23% | 1566.1 ± 199.9 NS | 1.211 | +20% |
| 16 | 1086.7 ± 213.6* | 2.506 | +99% | 1785.0 ± 292.2* | 2.196 | +53% | 1757.1 ± 209.8* | 2.248 | +35% |
| 32 | 1782.0 ± 161.7*** | 6.989 | +226% | 3070.0 ± 164.6*** | 9.779 | +162% | 3260.0 ± 121.7*** | 11.232 | +150% |
| RO 15-4513 2 mg/kg s.c. −30 min | 345.0 ± 59.4* | 2.160 | −37% | 681.0 ± 102.6** | 3.514 | −42% | 837.0 ± 116.7** | 3.194 | −36% |

TABLE 2b

| l-threo-Methylphenidate (mg/kg) s.c. −30 min | NUMBER OF CLONIC CONVULSIONS | | NUMBER OF TONIC CONVULSIONS | | NUMBER OF DEATHS | |
|---|---|---|---|---|---|---|
| | number of rats | % antagonism | number of rats | % antagonism | number of rats | % antagonism |
| 0 | 10 | — | 10 | — | 10 | — |
| 8 | 10 | 0% | 10 | 0% | 10 | 0% |
| 16 | 9 | 10% | 8 | 20% | 7 | 30% |
| 32 | 10 | 0% | 3++ | 70% | 3++ | 70% |
| RO 15-4513 2 mg/kg s.c. −30 min | 10 | 0% | 10 | 0% | 10 | 0% |
| DIAZEPAM 4 mg/kg s.c. −30 min | 0+++ | 100% | 0+++ | 100% | 0+++ | 100% |

TABLE 3

| TREATMENT (mg/kg) s.c. −30 min | NUMBER OF RATS SLEEPING | SLEEP DURATION (#) (min) | | |
|---|---|---|---|---|
| | | mean ± s.e.m. | t value | % change from control |
| 0 | 10 | 62.2 ± 12.4 | | |
| l-threo-Methylphenidate | | | | |
| 0.5 | 9 | 63.8 ± 18.5 NS | 0.072 | +3% |
| 2 | 4 + | 9.5 ± 6.4** | 3.777 | −85% |
| 4 | 6 | 4.3 ± 2.3*** | 4.589 | −93% |
| 8 | 1 +++ | 13.3 ± 13.3 | 2.688 | −79% |
| d-threo-Methylphenidate | | | | |
| 0.25 | 6 | 10.5 ± 5.3** | 3.830 | −83% |
| 0.5 | 8 | 21.6 ± 13.5* | 2.218 | −65% |
| 1 | 3 ++ | 2.1 ± 1.5*** | 4.810 | −97% |
| 2 | 0 ++ | 0.0 ± 0.0*** | 5.012 | −100% |
| dl-threo-Methylphenidate | | | | |
| 0.25 | 9 | 94.2 ± 18.3 NS | 1.445 | +51% |
| 0.5 | 8 | 50.2 ± 16.2 NS | 0.590 | −19% |
| 1 | 0 +++ | 0.0 ± 0.0*** | 5.012 | −100% |
| 2 | 4 + | 19.0 ± 12.6 | 2.449 | −70% |
| 4 | 0 +++ | 0.0 ± 0.0*** | 5.012 | −100% |
| Caffeine 16 mg/kg s.c. −30 min | 1 +++ | 0.5 ± 0.5*** | 4.968 | −99% |

The invention claimed is:

1. A method for treating a condition selected from the group consisting of convulsant states, bipolar disorder, wherein said method comprises administering to a patient in need of such treatment an effective amount of l-threo-methylphenidate in substantially single enantiomer form.

2. The method, according to claim 1, wherein the condition that is treated is epilepsy.

3. The method, according to claim 1, wherein the condition that is treated is bipolar disorder.

* * * * *